（12）United States Patent
Hassan et al.

(10) Patent No.: US 8,349,269 B2
(45) Date of Patent: Jan. 8, 2013

(54) HIGH SHEAR SYSTEM AND PROCESS FOR THE PRODUCTION OF ACETIC ANHYDRIDE

(75) Inventors: Abbas Hassan, Sugar Land, TX (US); Ebrahim Bagherzadeh, Sugar Land, TX (US); Rayford G. Anthony, College Station, TX (US); Gregory G. Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 28 days.

(21) Appl. No.: 12/976,165

(22) Filed: Dec. 22, 2010

(65) Prior Publication Data

US 2011/0091360 A1    Apr. 21, 2011

Related U.S. Application Data

(62) Division of application No. 12/136,508, filed on Jun. 10, 2008, now Pat. No. 7,919,645.

(60) Provisional application No. 60/946,476, filed on Jun. 27, 2007.

(51) Int. Cl.
    *B01J 19/18* (2006.01)
(52) U.S. Cl. .......... 422/225; 422/135; 366/342; 44/301; 44/302; 516/197
(58) Field of Classification Search .................. 422/135, 422/225; 366/364; 44/301, 302; 516/197
    See application file for complete search history.

(56) References Cited

U.S. PATENT DOCUMENTS

| | | | |
|---|---|---|---|
| 3,296,168 | A | 1/1967 | Jirik et al. |
| 3,781,320 | A | 12/1973 | Irwin |
| 3,813,421 | A | 5/1974 | McKelvey et al. |
| 3,892,798 | A | 7/1975 | Heeg et al. |
| 4,115,444 | A | 9/1978 | Rizkalla |
| 4,160,718 | A | 7/1979 | Rendall et al. |
| 4,252,983 | A | 2/1981 | Erpenbach et al. |
| 4,333,885 | A | 6/1982 | Feitler |
| 4,519,956 | A | 5/1985 | Lin et al. |
| 4,563,309 | A | 1/1986 | Wegman |
| 4,724,269 | A | 2/1988 | Suzki et al. |
| 4,886,905 | A | 12/1989 | Larkins, Jr. |
| 4,914,029 | A | 4/1990 | Caransa et al. |
| 4,950,831 | A | 8/1990 | Staton et al. |

(Continued)

FOREIGN PATENT DOCUMENTS

CA    1293465    12/1991

(Continued)

OTHER PUBLICATIONS

IKA—Rotor/Stator Generators—2003 Processing Catalog.*

(Continued)

*Primary Examiner* — Walter D Griffin
*Assistant Examiner* — Huy-Tram Nguyen
(74) *Attorney, Agent, or Firm* — Timothy S. Westby; Porter Hedges LLP

(57) ABSTRACT

A system and method for a high shear mechanical device incorporated into a process for the production of acetic anhydride as a reactor device is shown to be capable of decreasing mass transfer limitations, thereby enhancing the process. A system for the production of acetic anhydride including the mixing of catalyst and acetic acid via a high shear device.

20 Claims, 2 Drawing Sheets

U.S. PATENT DOCUMENTS

| | | | |
|---|---|---|---|
| 5,009,816 | A | 4/1991 | Weise et al. |
| 5,264,087 | A | 11/1993 | Lowery et al. |
| 5,382,358 | A | 1/1995 | Yeh |
| 5,451,348 | A | 9/1995 | Kingsley |
| 5,488,143 | A | 1/1996 | Uhm et al. |
| 5,538,191 | A | 7/1996 | Holl |
| 5,710,355 | A | 1/1998 | Krishnamurti |
| 5,756,714 | A | 5/1998 | Antrim et al. |
| 5,877,350 | A | 3/1999 | Langer et al. |
| 6,194,625 | B1 | 2/2001 | Graves et al. |
| 6,241,472 | B1 | 6/2001 | Bosch et al. |
| 6,251,289 | B1 | 6/2001 | Sherman |
| 6,368,366 | B1 | 4/2002 | Langer et al. |
| 6,368,367 | B1 | 4/2002 | Langer et al. |
| 6,383,237 | B1 | 5/2002 | Langer et al. |
| 6,395,935 | B1 * | 5/2002 | Baurmeister et al. ......... 568/302 |
| 6,530,964 | B2 | 3/2003 | Langer et al. |
| 6,693,213 | B1 | 2/2004 | Kolena et al. |
| 6,742,774 | B2 | 6/2004 | Holl |
| 6,768,021 | B2 | 7/2004 | Horan et al. |
| 6,787,036 | B2 | 9/2004 | Long |
| 6,809,217 | B1 | 10/2004 | Colley et al. |
| 7,119,263 | B1 | 10/2006 | Chen |
| 7,199,263 | B2 | 4/2007 | Warner |
| 7,919,645 | B2 | 4/2011 | Hassan et al. |
| 2003/0043690 | A1 | 3/2003 | Holl |
| 2004/0052158 | A1 | 3/2004 | Holl |
| 2005/0033069 | A1 | 2/2005 | Holl et al. |
| 2006/0196812 | A1 | 9/2006 | Beetge et al. |
| 2006/0245991 | A1 | 11/2006 | Holl et al. |
| 2006/0260980 | A1 | 11/2006 | Yeung |
| 2006/0272634 | A1 | 12/2006 | Nehmer et al. |
| 2007/0030322 | A1 | 2/2007 | Lee et al. |
| 2008/0135253 | A1 | 6/2008 | Vinegar et al. |
| 2008/0245705 | A1 | 10/2008 | Siskin et al. |
| 2009/0095480 | A1 | 4/2009 | Vinegar et al. |
| 2009/0323458 | A1 | 12/2009 | Fischer et al. |

FOREIGN PATENT DOCUMENTS

| | | |
|---|---|---|
| CA | 2200899 | 9/1998 |
| CA | 2232929 | 5/2004 |
| CA | 2353109 | 12/2005 |
| EA | 014897 | 2/2011 |
| EP | 1604969 A | 12/2005 |
| JP | 61183235 A | 8/1986 |
| JP | 2000143706 A | 5/2000 |
| JP | 2002003505 A | 1/2002 |
| JP | 2002121353 A | 4/2002 |
| JP | 2007505201 A | 3/2007 |
| WO | 9843725 A | 10/1998 |
| WO | 2002064708 A2 | 8/2002 |
| WO | 2005108533 A2 | 11/2005 |
| WO | 2007023864 Y | 3/2007 |

OTHER PUBLICATIONS

Rotor/Stator for Batch, In-Line Mixing by IKA—Apr. 14, 2010.*
Gogate et al., "Cavitation: A technology on the horizon," Current Science 91 (No. 1): 35-46 (2006).
Search Report for PCT/US2008/066582 dated Apr. 18, 2011.
Canadian Office Action dated Feb. 17, 2011.
Office Action Dated Apr. 20, 2010 for U.S. Appl. No. 12/411,660.
Office Action Dated Apr. 20, 2010 for U.S. Appl. No. 12/427,286.
Office Action Dated Apr. 23, 2010 for U.S. Appl. No. 12/568,155.
Office Action Dated Apr. 27, 2010 for U.S. Appl. No. 12/568,280.
Office Action Dated May 5, 2010 for U.S. Appl. No. 12/142,120.
Office Action Dated Jun. 25, 2009 for U.S. Appl. No. 12/142,447.
Office Action Dated Jan. 7, 2010 for U.S. Appl. No. 12/142,447.
Office Action Dated May 13, 2010 for U.S. Appl. No. 12/142,447.
Office Action Dated Feb. 4, 2010 for U.S. Appl. No. 12/492,721.
Office Action Dated Feb. 18, 2010 for U.S. Appl. No. 12/635,433.
Office Action Dated Feb. 18, 2010 for U.S. Appl. No. 12/635,454.
Office Action Dated May 14, 2010 for U.S. Appl. No. 12/137,441.
Office Action Dated Feb. 19, 2010 for U.S. Appl. No. 12/144,459.
Office Action Dated Sep. 2, 2009 for U.S. Appl. No. 12/142,433.
Office Action Dated Jan. 29, 2010 for U.S. Appl. No. 12/142,433.
Office Action Dated May 24, 2010 for U.S. Appl. No. 12/142,433.
Office Action Dated Apr. 30, 2010 for U.S. Appl. No. 12/141,191.
Office Action Dated Oct. 27, 2009 for U.S. Appl. No. 12/142,120.
Office Action Dated May 5, 2010 for U.S. Appl. No. 12/571,537.
Office Action Dated Jul. 28, 2010 for U.S. Appl. No. 12/635,433.
International Application No. PCT/US2008/068161 International Search Report dated Sep. 24, 2008, 7 pages.
Office Action dated Jun. 3, 2011 for U.S. Appl. No. 12/568,280.
Office Action dated Jun. 2, 2011 for U.S. Appl. No. 12/427,286.
Office Action dated Jun. 3, 2011 for U.S. Appl. No. 12/568,155.
Office Action dated Feb. 29, 2012 for U.S. Appl. No. 12/146,733.
Office Action dated Feb. 24, 2011 for U.S. Appl. No. 12/796,358.
Gulf Cooperation Council Notice of Publication dated Oct. 20, 2012 for corresponding Gulf Cooperation Council Application No. GCC/P/2008/11142 (1 pg.).
Gulf Cooperation Council Examination Report dated Jul. 8, 2011 for corresponding Gulf Cooperation Council Application No. GCC/P/2008/11142 (4 pgs.).
Canadian Notice of Allowance dated Aug. 2, 2012 for corresponding Canadian Application No. 2,682,097(1 pg.).
Canadian Office Action dated Nov. 1, 2011 for corresponding Canadian Application No. 2,682,097(2 pg.).
European Seach Report dated Apr. 18, 2011 for corresponding European Application No. 08770729.5 (4 pgs.).

* cited by examiner

HIGH SHEAR SYSTEM AND PROCESS FOR THE PRODUCTION OF ACETIC ANHYDRIDE

CROSS-REFERENCE TO RELATED APPLICATIONS

This application is a divisional application of U.S. Ser. No. 12/136,508 filed on Jun. 10, 2008, now U.S. Pat. No. 7,919,645, which claims the benefit under 35 U.S.C. §119(e) of U.S. Provisional Patent Application No. 60/946,476 filed Jun. 27, 2007, the disclosures of which are hereby incorporated herein by reference for all purposes.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of acetic anhydride and more particularly, to apparatus and methods enhancing the production of acetic anhydride. More specifically, the disclosure relates to the reduction of mass transfer limitations of apparatus and methods for the production of acetic anhydride.

2. Background of the Invention

Acetic anhydride is an industrial chemical reagent, widely used in organic synthesis. Furthermore, large quantities are used, for example, in the manufacture of cellulose acetate as well as other commercially significant acetylations. It has commonly been produced on an industrial scale by the reaction of ketene and acetic acid. Conventionally processes for preparing acetic anhydride have been disclosed in U.S. Pat. Nos. 4,115,444; 4,252,983; 4,333,885; 4,519,956; 4,563,309; and 5,488,143.

U.S. Pat. No. 7,199,263 describes a process for co-production of acetic anhydride and acetate co-production. The production of acetic anhydride by the ketene process is conventionally known. The method comprises the thermal decomposition of acetic acid at high temperatures utilizing, for example, triethyl phosphate dehydration catalyst to produce ketene (1) which is subsequently reacted with excess acetic acid to obtain acetic anhydride (2):

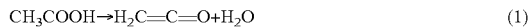

$$CH_3COOH \rightarrow H_2C=C=O + H_2O \quad (1)$$

$$H_2C=C=O + CH_3COOH \rightarrow O=CCH_3OCH_3C=O \quad (2)$$

Reaction (1) is carried out at low pressure and elevated temperature, typically in excess of 700° C. Catalyst in the product stream may be neutralized with ammonia. The process is widely employed however, it is capital intensive. For efficient acetic anhydride production, water generated in reaction (1) is removed and acetic acid is recovered. Due to the quantity of water, 1 mole of water per mole of ketene, weak acid recovery adversely impacts operating energy costs.

Accordingly, there is a need in the industry for improved processes for the production of acetic anhydride whereby water removal and acid recovery are increased, so that production of acetic anhydride is more commercially feasible.

SUMMARY OF THE INVENTION

A high shear system and method for accelerating the production of acetic anhydride is disclosed. The disclosed high shear method reduces mass transfer limitations, thereby improving reaction conditions in the reactor such as the reaction rate, temperature, pressure, time and/or product yield. In accordance with certain embodiments of the present disclosure, a method is provided that makes possible an increase in the rate of acetic anhydride production by providing for more optimal time, temperature and pressure conditions than are conventionally used.

The method employs a high shear device to provide enhanced time, temperature and pressure conditions resulting in accelerated chemical reactions between reactants.

These and other embodiments, features and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
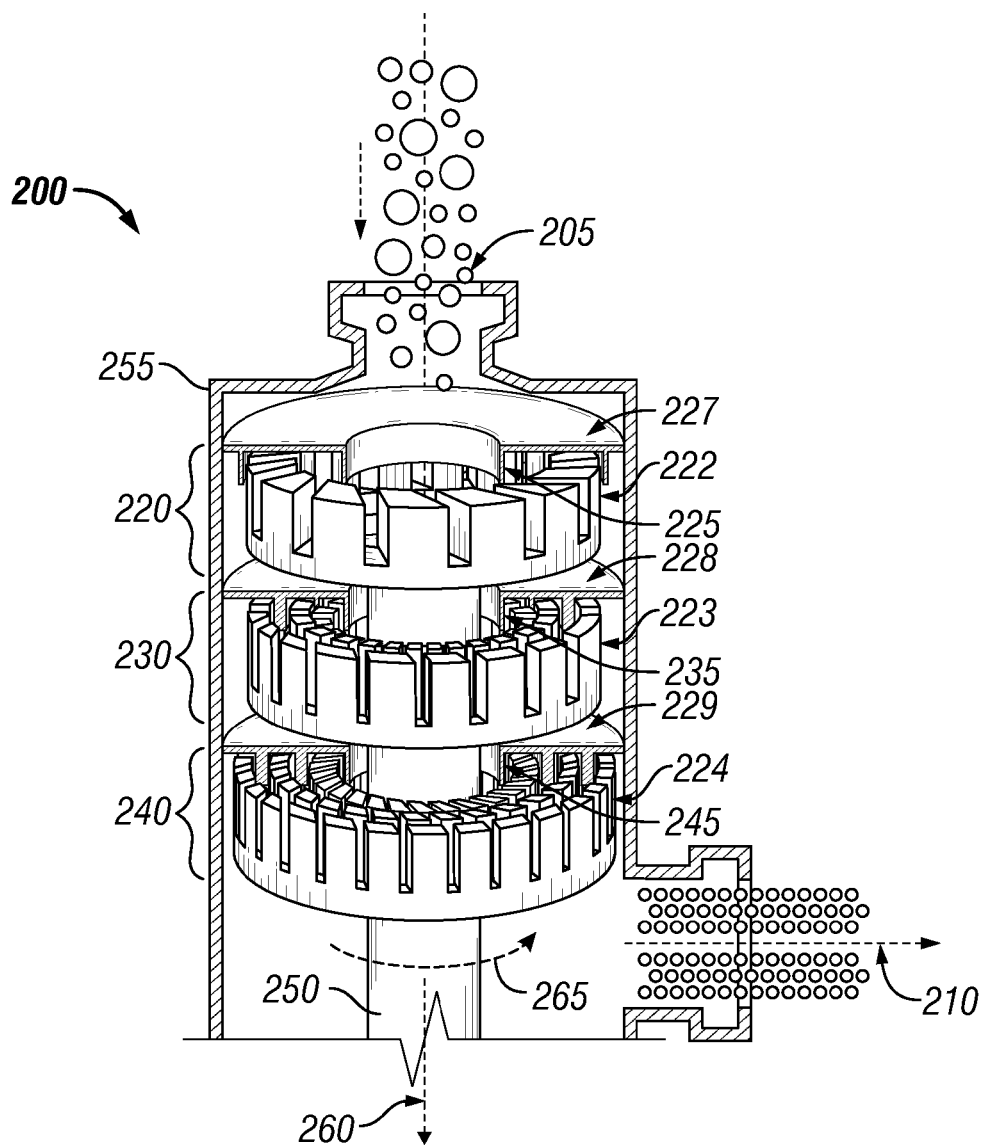
FIG. 1 is a cross-sectional diagram of a high shear device for the production of acetic anhydride.

A system and method employs an external high shear mechanical device to provide rapid contact and mixing of chemical ingredients in a controlled environment in the reactor/mixer device. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants.

In conventional reactors, contact time for the reactants and/or catalyst is often controlled by mixing which provides contact with two or more reactants involved in a chemical reaction. A reactor assembly that comprises an external high shear mixer makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

High Shear Device

High shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 μm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 μm to about 1 μm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 μm to about 25 μm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 μm; preferably the bubbles are sub-micron in diameter. In certain instances, the average bubble size is in the range from about 1.0 μm to about 0.1 μm. Alternatively, the average bubble size is less than about 400 nm (0.4 μm) and most preferably less than about 100 nm (0.1 μm).

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec)

=π·D·n, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, 2 π R, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The high shear device 200 combines high tip speeds with a very small shear gap to produce significant shear on the material. The amount of shear is typically dependent on the viscosity of the fluid. The shear rate generated in a high shear device 200 may be greater than 20,000 s$^{-1}$. In embodiments, the shear rate generated is in the range of from 20,000 s$^{-1}$ to 100,000 s$^{-1}$.

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 μm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate the acetic acid into free radicals exposed to catalysts for the formation of ketene, which then form corresponding acetic anhydride product.

Figure 2:
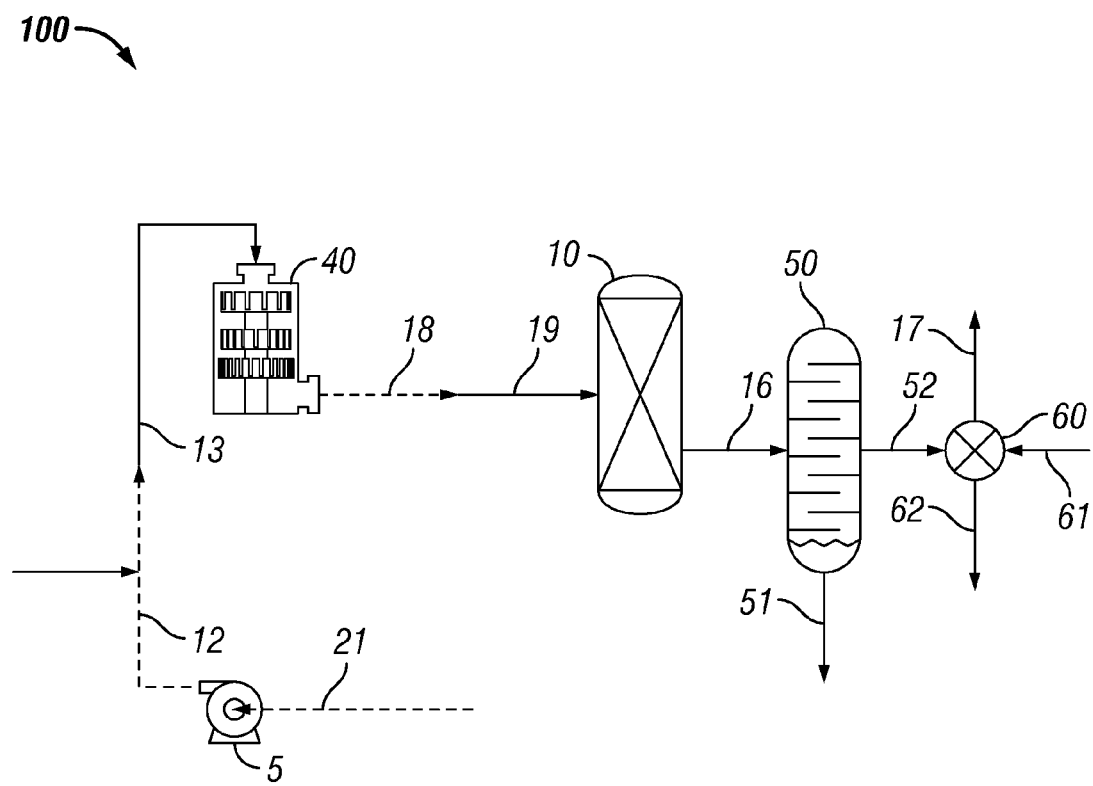
FIG. 2 is a process flow diagram according to an embodiment of the present disclosure for a high shear system for production of acetic anhydride.

Description of High Shear System and Process for the Production of Acetic Anhydride The high shear acetic anhydride production process and system of the present disclosure will now be described in relation to FIG. 2 which is a flow diagram of representative high shear system 100 comprising high shear device 40. FIG. 2 illustrates the basic components of the high shear system 100 including pump 5, high shear device (HSD) 40, and ketene production reactor 10. The high shear device 40 is positioned between pump 5 and reactor 10. High shear system 100 may further comprise chiller train 50 and acetic anhydride production reactor 60.

Pump 5 is used to provide a controlled flow throughout high shear device 40 and high shear acetic anhydride production system 100. Pump inlet stream 21 is a liquid comprising acetic acid is introduced to pump 5. Pump 5 increases the pressure of the pump inlet stream 21 to greater than about 203 kPa (about 2 atm); alternatively, the inlet stream 21 is pressurized to greater than about 304 kPa (about 3 atm). Additionally, pump 5 may build pressure throughout HSS 100. In this way, HSS 100 combines high shear with pressure to enhance reactant intimate mixing. Preferably, all contact parts of pump 5 are stainless steel, for example, 316 stainless steel. Pump 5 may be any suitable pump, for example, a Dayton Pressure Booster Pump Model 2P372E, Dayton Electric Co (Niles, Ill.).

The pressurized liquid acetic acid exits pump 5 via pump exit stream 12. Pump exit stream 12 is in fluid communication with HSD inlet stream 13. In certain instances, dispersible liquid stream 22 comprising a liquid catalyst is introduced to HSD inlet stream 13. Dispersible reactant stream 22 comprises a liquid dehydration catalyst. Any suitable dehydration catalyst known to those of skill in the art may be employed. In certain instances, the catalyst in dispersible reactant stream 22 comprises triethyl phosphate dehydration catalyst. In alternative embodiments, liquid catalyst dispersible reactant stream 22 comprises diammonium phosphate dehydration catalyst.

The HSD inlet stream 13 comprising a mixing of dispersible liquid stream 22 and pressurized pump exit stream 12 may initiate reaction (1). In further instances, pump exit stream 12 and dispersible liquid stream 22 are introduced separately into HSD inlet stream 13. HSD inlet stream 13 feeds the dispersible reactant stream 22 and the pump exit stream 12 to the HSD 40.

High shear device 40 serves to intimately mix the pressurized liquid acetic acid solution comprising pump outlet stream 12 with the liquid catalyst comprising dispersible reactant stream 22. There may be a plurality of high shear devices 40 used in series, or in parallel, as known to one skilled in the art. As discussed in detail above, the high shear device 40 is a mechanical device that utilizes, for example, a stator rotor mixing head with a fixed gap between the stator and rotor. HSD 40 combines high tip speeds with a very small shear gap to produce significant shear on the material being processed. The amount of shear will be dependant on the viscosity of the fluid.

An emulsion of catalyst and acetic acid is formed in high shear device 40. As previously described, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof. In certain instances, the emulsion comprises liquid acetic acid as the continuous phase and the catalyst as the dispersible phase.

The resultant emulsion comprises microglobules, or globules in the submicron size. In embodiments, the resultant emulsion has an mean globule diameter of less than about 1.5 μm, preferably the mean globule diameters is from about 0.4 μm (400 nm) to about 1.5 μm. In certain instances, the high shear mixing produces hydroglobules capable of remaining dispersed at atmospheric pressure for about 15 minutes. The high shear treatment of the catalyst and the acetic acid in the emulsion may initiate reaction (1). In certain embodiments, most of the reaction occurs within the HSD 40.

HSD 40 is in fluid communication with reactor 10. High shear device (HSD) outlet stream 18 comprises an emulsion of micron and/or submicron-sized globules, as discussed hereinabove. HSD outlet stream 18 is fluidly connected to reactor inlet stream 19. HSD outlet stream and reactor inlet stream 19 may be the same stream. In certain instances, the HSD outlet stream 18 may be further processed before entering reactor inlet stream 19. Alternatively, HSD outlet stream 18 may be recycled through the HSD 40 prior to introduction to reactor inlet stream 19.

Reactor inlet stream 19 is in fluid communication with reactor 10. Reactor inlet stream 19 enters reactor 10 wherein further ketene production occurs according to reaction (1). Reactor 10 is any reactor suitable for the pyrolysis of acetic acid at high temperatures to produce ketene. Reactor 10 is operated at near atmospheric pressure. Further, reactor 10 may be used for cooling of fluid, wherein the reaction (1) occurs in high shear device 40.

The acetic acid pyrolysis tubes of reactor 10 comprise nickel-free alloys, e.g. ferrochrome alloy, chrome-aluminum steel, because nickel promotes the formation of soot and coke, and reacts with carbon monoxide yielding a highly toxic metal carbonyl. Coke efficiency represents an efficiency loss. Conventional operating conditions furnish about 85 to about 88% conversion, with selectivity to ketene between about 90 mol % and about 95 mol %. Furthermore, heterogeneous processes using a fixed or slurry catalyst bed of phosphoric acid derivatives and phosphates is utilized at lower temperatures to avoid deactivating the catalyst and coking the catalyst and reactor. In embodiments, the conversion, the efficiency, and/or both are improved by the process and system of HSS 100.

The heat of reaction (1) is approximately 147 kJ/mol. Optimum yields of ketene conventionally require a temperature of from about 680° C. to about 750° C. Low pressure increases the yield, but not the efficiency of the acetic acid pyrolysis. In embodiments, the process comprising a high shear device 40 for reactant mixing allows for use of lower temperatures in reactor 10 during pyrolysis. The reaction contained in the reactor 10 yields ketene and is removed from the reactor in ketene product stream 16.

Removing the water by condensation prior to forming acetic anhydride is an important step in the process. Ketene product stream 16 is processed for conversion to acetic anhydride. Ketene product stream 16 comprising water enters chiller train 50. Chiller train 50 condenses water and acetic acid from the hot furnace gases in ketene product stream 16. The catalyst, e.g. triethyl phosphate, is neutralized in the gases of ketene product stream 16 with ammonia. The process condensate 51 from chiller train 50 comprises primarily acetic acid, water, acetic anhydride, and non-volatiles including phosphorus-containing catalyst (e.g., ammonium phosphates) and carbon from furnace coking and ketene decomposition. Process condensate 51 may be recycled through HSS 100. Additionally, overhead may be further purified, recycled, or otherwise utilized.

Uncondensed output stream 52 from chiller train 50 is fed to anhydride reactor 60. In reactor 60, ketene is reacted with additional acetic acid stream 61 to produce crude liquid acetic anhydride stream 62 per reaction (2). In embodiments, use a HSS 100 comprising reactant mixing by a high shear device 40 allows use of lower temperature and/or pressure in reactor 10 than previously enabled. The method comprises incorporating high shear device 40 into an established process. Incorporation of HSD 40 improves the operating conditions such as temperature, pressure, rate and production of the HSS 100 in comparison to a process or system operated without high shear device 40.

The application of enhanced mixing of the reactants by high shear device 40 potentially causes greater conversion of acetic acid to ketene in some embodiments of the process. Further, the enhanced mixing of the reactants potentiates an increase in throughput of the process stream of the high shear system 100. In certain instances, the high shear device 40 is incorporated into an established process, thereby enabling an increase in production (i.e., greater throughput).

In embodiments, the method and system of this disclosure enable design of a smaller and/or less capital intensive process allowing selection of a reactor 10 having lower operating temperature and/or pressure capability than previously possible without the incorporation of high shear device 40. In embodiments, the disclosed method reduces operating costs/increases production from an existing process. Alternatively, the disclosed method may reduce capital costs for the design of new processes. Potential benefits of the present disclosure include, but are not limited to, faster cycle times, increased throughput, reduced operating costs and/or reduced capital expense due to the possibility of designing smaller reactors, more effective utilization of catalyst and/or operating the ketene reactor at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A system for the production of acetic anhydride, comprising:
   a pump positioned upstream of a dispersible liquid catalyst inlet;
   at least one high shear device, fluidly connected to the outlet of the pump, configured for producing an emulsion of the liquid catalyst in liquid acetic acid, wherein said at least one high shear device is configured to produce an emulsion having an average catalyst globule diameter of less than about 5 µm; and
   a pyrolysis reactor fluidly connected to an outlet of the at least one high shear device, wherein said pyrolysis reactor is configured to produce ketene by thermal decomposition of acetic acid.

2. The system of claim 1 wherein the at least one high shear device comprises at least one shear generator configured for producing a tip speed of at least 5 m/s.

3. The system of claim 2 wherein the at least one high shear device has a nominal tip speed of at least about 23 m/s.

4. The system of claim 2 wherein the at least one high shear device produces a localized pressure at the tip of at least about 1000 MPa.

5. The system of claim 2 wherein the at least one high shear device is configured to produce a shear rate of greater than about 20,000 s$^{-1}$.

6. The system of claim 2 wherein the at least one high shear device is configured for an energy expenditure of at least 1000 W/m$^3$.

7. The system of claim 1 wherein the at least one high shear device is configured for producing an emulsion with a mean globule diameter of less than about 1.5 µm.

8. The system of claim 1 further comprising at least one heat transfer element fluidly connected with the pyrolysis reactor.

9. The system of claim 8 wherein the heat transfer element comprises a chiller configured for condensing acetic acid, water, and ammonia-neutralized catalyst from a gas stream comprising ketene.

10. A system for the production of acetic anhydride, the system comprising:
    a high shear device, having at least one shear generator, at least one inlet, and an outlet;
    a pump fluidly connected to the inlet of the high shear device;
    an acetic acid stream fluidly connected to the pump;
    a liquid catalyst stream fluidly connected to the high shear device; and
    a pyrolysis reactor fluidly connected to the outlet of the high shear device.

11. The system of claim 10, wherein the high shear device comprises a plurality of rotor-stator shear generators.

12. The system of claim 11, wherein each rotor-stator is configured to produce a different amount of shear.

13. The system of claim 10, wherein the high shear device is configured to produce a shear rate of greater than about 20,000 s$^{-1}$.

14. The system of claim 10 wherein the at least one high shear device is configured for an energy expenditure of at least 1000 W/m$^3$.

15. The system of claim 10, wherein the pyrolysis reactor is configured to produce ketene by thermal decomposition of acetic acid in an emulsion with a mean globule diameter of less than about 1.5 µm.

16. A system for the production of acetic anhydride, comprising:
    a high shear device configured to process liquid catalyst and liquid acetic acid, wherein the high shear device operates to produce an emulsion of liquid catalyst and liquid acetic acid, and wherein the emulsion has an average catalyst globule diameter of less than about 5 µm;
    a reactor fluidly connected to an outlet of the high shear device, wherein the reactor is operable at conditions to promote a reaction of acetic acid in the emulsion that produce a product stream comprising ketene; and
    a second reactor fluidly connected with the reactor, wherein at least part of the product stream is transferred to the second reactor, and wherein at least some ketene in the second reactor reacts to produce acetic anhydride.

17. The system of claim 16, wherein the liquid catalyst is triethyl phosphate.

18. The system of claim 16, wherein the reaction of acetic acid is a heterogeneous catalytic reaction.

19. The system of claim 16, wherein the at least one high shear device comprises a rotor and a stator.

20. The system of claim 19, wherein the at least one high shear device is operable to produce a localized pressure at a tip of the rotor of at least about 1000 MPa.

* * * * *